(12) United States Patent
Piergentini

(10) Patent No.: US 12,397,098 B2
(45) Date of Patent: Aug. 26, 2025

(54) MACHINE FOR THE EXTRACORPOREAL PHOTOPHERESIS OF A BIOLOGICAL FLUID

(71) Applicant: PELHAM CRESCENT S.R.L., Perugia (IT)

(72) Inventor: Marco Piergentini, Perugia (IT)

(73) Assignee: PELHAM CRESCENT S.R.L., Perugia (IT)

( * ) Notice: Subject to any disclaimer, the term of this patent is extended or adjusted under 35 U.S.C. 154(b) by 502 days.

(21) Appl. No.: 17/798,710

(22) PCT Filed: Feb. 16, 2021

(86) PCT No.: PCT/IB2021/051292
§ 371 (c)(1),
(2) Date: Aug. 10, 2022

(87) PCT Pub. No.: WO2021/165827
PCT Pub. Date: Aug. 26, 2021

(65) Prior Publication Data
US 2023/0125686 A1    Apr. 27, 2023

(30) Foreign Application Priority Data
Feb. 19, 2020   (IT) .................. 102020000003407

(51) Int. Cl.
*A61M 1/36* (2006.01)
*A61M 1/34* (2006.01)

(52) U.S. Cl.
CPC ........ *A61M 1/3683* (2014.02); *A61M 1/3496* (2013.01)

(58) Field of Classification Search
CPC .............. A61M 1/3496; A61M 1/3681; A61M 1/3683; A61M 2205/053; A61M 1/16;
(Continued)

(56) References Cited

U.S. PATENT DOCUMENTS

| 4,573,962 A | 3/1986 | Troutner |
| 6,190,609 B1 * | 2/2001 | Chapman ............ A61M 1/3683 435/283.1 |

(Continued)

FOREIGN PATENT DOCUMENTS

| EP | 1 576 973 A1 | 9/2005 |
| EP | 1 867 355 A1 | 12/2007 |
| WO | WO 96/22117 A2 | 7/1996 |

OTHER PUBLICATIONS

Hermetically Sealed | English meaning - Cambridge Dictionary https://dictionary.cambridge.org/dictionary/english/hermetically-sealed#google_vignette (Year: 2025).*

(Continued)

*Primary Examiner* — Adam Marcetich
(74) *Attorney, Agent, or Firm* — ASLAN LAW, P.C.

(57) ABSTRACT

A machine comprising a load-bearing body intended to receive a circuit for the extracorporeal circulation of a biological liquid, where the circuit comprises at least one bag containing the biological liquid, at least one collection container of the biological liquid to be treated, at least one transit duct of the biological liquid connected to at least the bag and to the collection container; a pumping unit/device/component/etc. of the biological liquid crossing the transit duct; an irradiation unit/device/component/etc. by way of UVA rays of the collection container; and at least one containment box defining a containment volume intended to house the collection container and at least one safety chamber arranged below the containment volume and communicating therewith, to collect any possible spillage of the biological liquid from the collection container where the safety chamber has at least one bottom wall and two side walls at which it is hermetically sealed.

13 Claims, 4 Drawing Sheets

(58) Field of Classification Search
CPC .......... A61M 1/3696; A61M 2205/051; A61M 2205/12; A61M 1/303; A61M 1/3686; A61M 2205/75; A61M 1/3616; A61L 2/24; A61L 2202/22; A61L 2/0047; A61L 2202/122; A61N 5/062; A61J 1/10; A61J 1/12

See application file for complete search history.

(56) References Cited

U.S. PATENT DOCUMENTS

| | | | |
|---|---|---|---|
| 6,491,656 B1 | 12/2002 | Morris | |
| 2002/0115585 A1* | 8/2002 | Hei | A61L 2/0035 |
| | | | 422/68.1 |
| 2003/0165398 A1* | 9/2003 | Waldo | A61L 2/087 |
| | | | 604/20 |
| 2003/0214874 A1* | 11/2003 | Hlavinka | B01F 33/055 |
| | | | 366/214 |
| 2005/0277863 A1* | 12/2005 | Davidner | A61M 1/3472 |
| | | | 604/6.08 |
| 2010/0178200 A1* | 7/2010 | Walker | A61L 2/10 |
| | | | 250/354.1 |
| 2014/0319035 A1* | 10/2014 | Burbank | A61M 1/1692 |
| | | | 73/40.5 R |
| 2016/0235906 A1* | 8/2016 | Takuwa | A61J 1/22 |
| 2016/0271310 A1* | 9/2016 | Iske | A61B 5/022 |
| 2017/0029776 A1* | 2/2017 | Cork | A61M 1/3681 |
| 2019/0041308 A1* | 2/2019 | Schryver | G01N 1/44 |
| 2019/0342947 A1* | 11/2019 | Shavit | B01F 31/23 |
| 2020/0030790 A1* | 1/2020 | Dodd | A61M 1/0209 |
| 2020/0188685 A1* | 6/2020 | Coultas | A61M 1/3681 |

OTHER PUBLICATIONS

Hermetic seal—definition of Hermetic seal by The Free Dictionary https://www.thefreedictionary.com/Hermetic+seal (Year: 2025).*

* cited by examiner

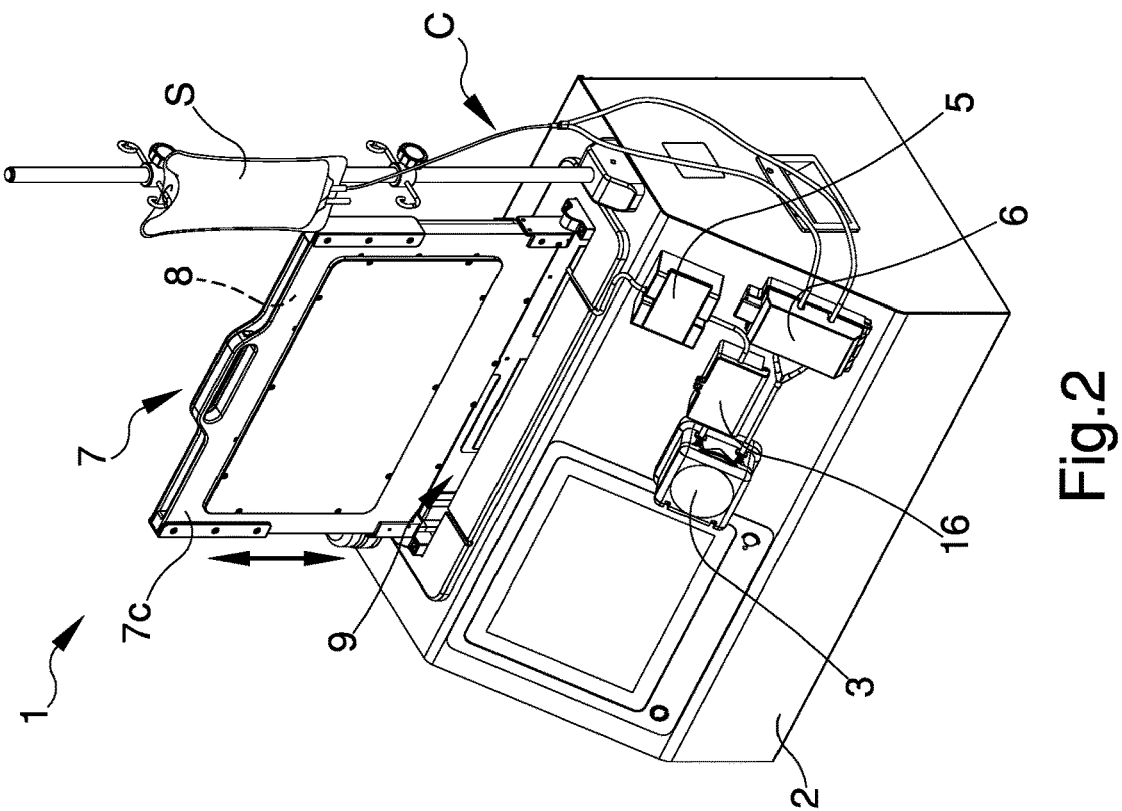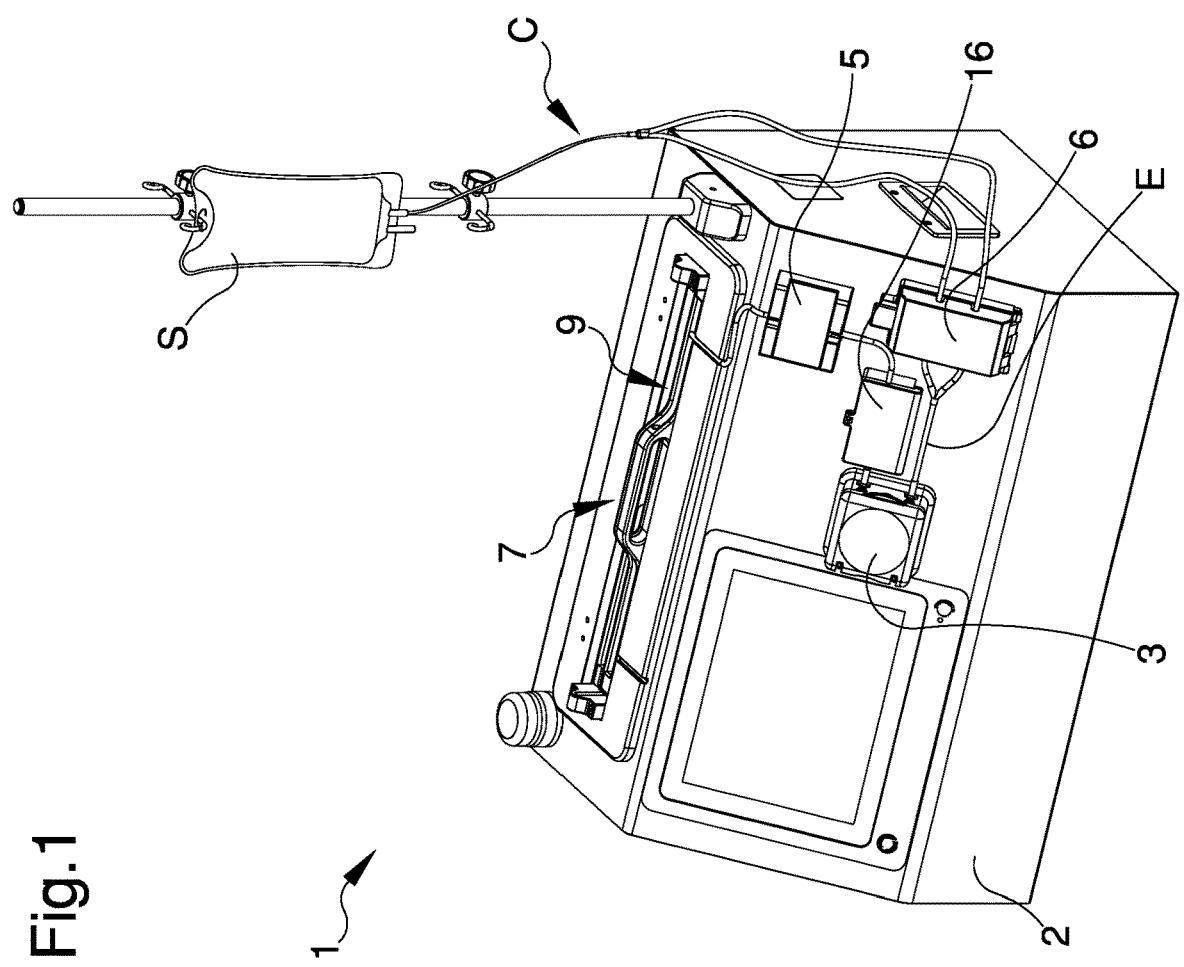

MACHINE FOR THE EXTRACORPOREAL PHOTOPHERESIS OF A BIOLOGICAL FLUID

CROSS-REFERENCE TO RELATED APPLICATIONS

This application claims priority to IT Patent Application No. 102020000003407 filed on Feb. 19, 2020, and this application claims priority to and is a 371 of international PCT Application No. PCT/IB2021/051292 filed on Feb. 16, 2021, the entire contents of which are hereby incorporated by reference.

TECHNICAL FIELD

The present invention relates to a machine for the extracorporeal photopheresis of a biological liquid, particularly blood or fractions thereof.

BACKGROUND ART

Extracorporeal photopheresis (ECP) is a therapy capable of modifying the immune reactions of an organism (hence it is called immune-modulatory therapy) and the first phase of the therapy consists in the separation of leukocytes from blood by centrifugal action, known in the medical field under the term of leukapheresis; the separation is intended to collect a cellular concentrate of lymphocytes and mononuclear cells.

The second phase of photopheresis consists of adding, to the collected cells, a light-sensitive drug and of exposing the whole to UVA-type ultraviolet light; the photo-sensitive drug used is a psoralen and the preferred and currently used drug is 8-methoxypsoralen (8-MOP).

At the end of the two aforementioned phases of which photopheresis is composed, the cell suspension with the photo-activated drug is reinfused to the patient and therefore it is clear that, in this case, the photopheresis is extracorporeal and autologous.

Currently, the practice of extracorporeal photopheresis is used in the treatment of several important diseases in order to facilitate and stimulate a mediated and tolerizing immune response: as well as in the case of skin T-cell lymphoma, also in the case of rejection following bone marrow transplantation, transplantation of solid organs such as heart, lung, liver, and kidney and in autoimmune diseases such as progressive systemic sclerosis, rheumatoid arthritis, psoriatic arthritis and systemic erythematosus lupus.

As far as known documents dealing with photopheresis of blood and its derivatives are concerned, note the following documents: U.S. Pat. Nos. 4,573,962, 6,491,656, EP 1 576 973 and EP 1 867 355.

The teachings of U.S. Pat. No. 4,573,962 relate to a device adapted to irradiate blood for the purpose of photo-activating a reagent substance mixed with blood, the device being also adapted to reinfuse the irradiated blood into the patient.

U.S. Pat. No. 6,491,656 describes and claims a device adapted to control the movements of liquids during extracorporeal blood treatment. Said device comprises an enclosure comprising a cavity into which converge both a plurality of inlets and outlets, the inlets being adapted to convey liquid inside the enclosure, the outlets being used for the treated liquid. Inside the enclosure are at least one valve and one filtering element.

EP 1 576 973 relates to an apparatus adapted to irradiate blood and comprising the possibility of allowing external irradiation dosages thanks to the intervention of a processor; in the device, a bag is used provided with meandering channels whose feeder tube is placed, in the outlet section, upstream of a pump and the diverter tube of which is placed at the point where the inlet of a recirculation bag is located.

EP 1 867 355, filed by the same applicant, describes a piece of photopheresis equipment comprising an irradiation chamber inside which the container of biological liquid to be irradiated is placed, an accumulation container for intermediate blood storage, an incubation container connected to the storage tank, and a plurality of ducts for the containment and conveyance of the biological liquid.

The equipment described by EP 1 867 355 further comprises closure means operable to control the flow of the biological liquid through the ducts and containers, an optical hematocrit level reader, pressure sensors, and liquid presence sensors adapted to detect any leakage of liquid from the containers.

These devices of known type, with particular reference to EP 1 867 355, do have some drawbacks.

In particular, they do not allow protecting the components of the relevant equipment in case of breakage of the biological liquid container and, therefore, of spillage of the liquid itself and consequent contamination of the electrical and electronic components.

Another drawback of these known types of equipment is that it is difficult to readily detect any breakage of the biological liquid container.

DESCRIPTION OF THE INVENTION

The main aim of the present invention is to devise a machine for the extracorporeal photopheresis of a biological liquid which allows protecting the components thereof, thus avoiding their contamination, in case of breakage of the container of the biological liquid to be treated.

Within this aim, one object of the present invention is to effectively and timely detect any spillage of the biological liquid from the relevant container.

Another object of the present invention is to devise a machine for the extracorporeal photopheresis of a biological liquid which allows overcoming the aforementioned drawbacks of the prior art within a simple, rational, easy, effective to use and low cost solution.

The objects set out above are achieved by the present machine for the extracorporeal photopheresis of a biological liquid according to claim 1.

BRIEF DESCRIPTION OF THE DRAWINGS

Other characteristics and advantages of the present invention will become more evident from the description of a preferred, but not exclusive, embodiment of a machine for the extracorporeal photopheresis of a biological liquid, illustrated by way of an indicative, yet non-limiting example, in the accompanying tables of drawings wherein:

FIG. 1 is an axonometric view of a machine according to the invention with the containment box in the operating position;

FIG. 2 is an axonometric view of the machine in FIG. 1 with the containment box in an insertion/removal position;

EMBODIMENTS OF THE INVENTION

Figure 3:
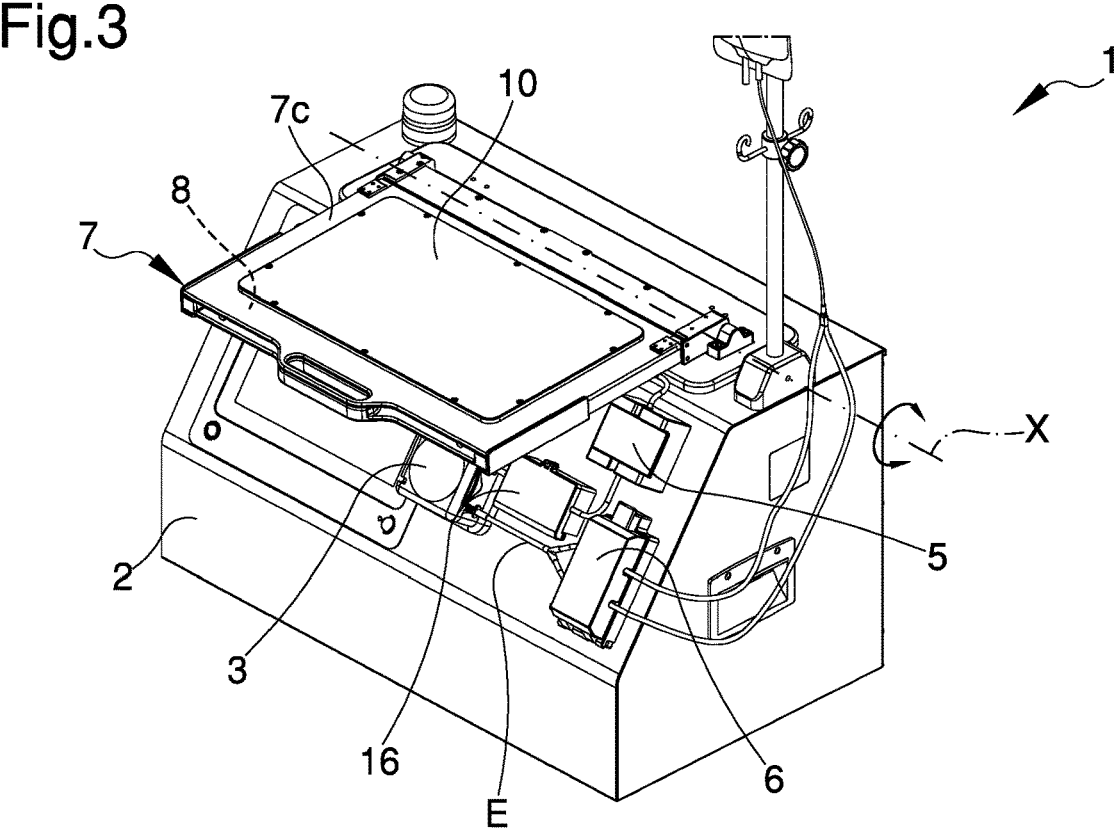
FIG. 3 is an axonometric view of the machine in FIG. 1 with the containment box in an additional insertion/removal position.
Figure 4:
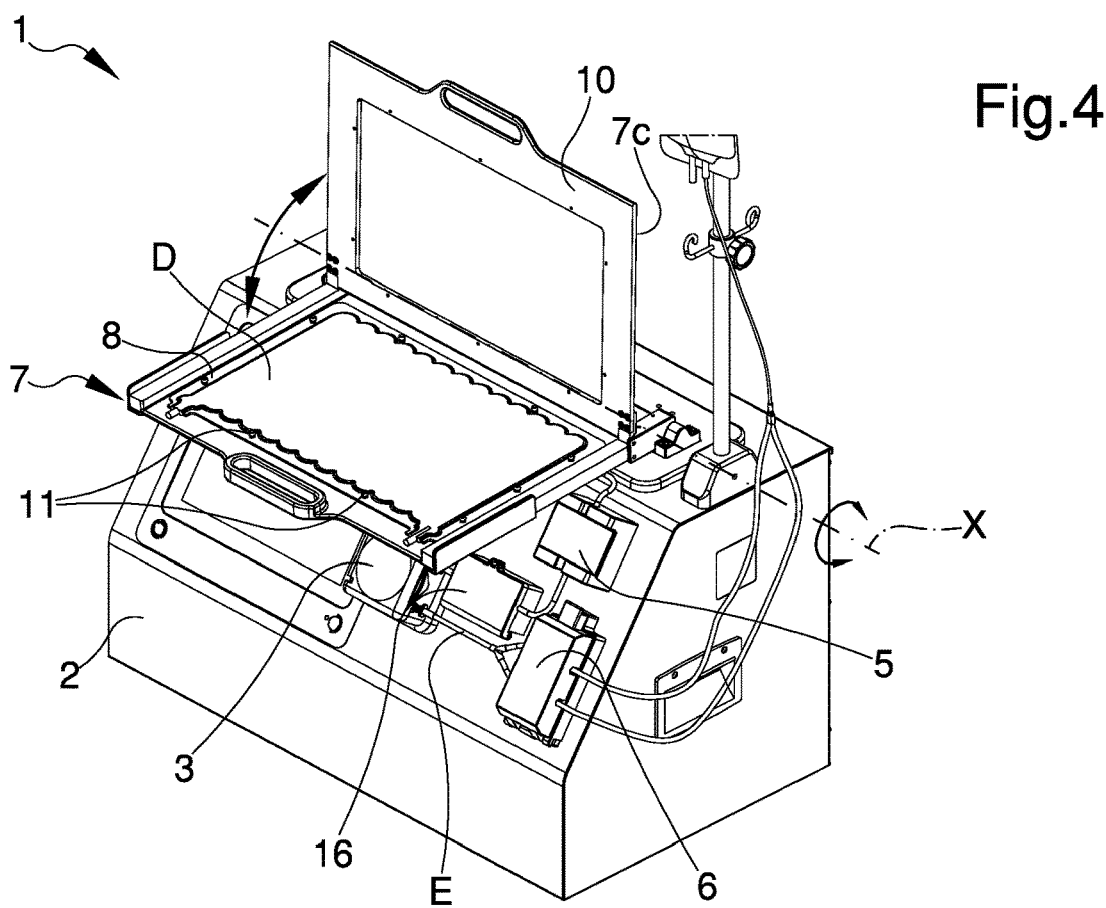
FIG. 4 is an axonometric view of the machine in FIG. 3 with the containment box open.
Figure 5:
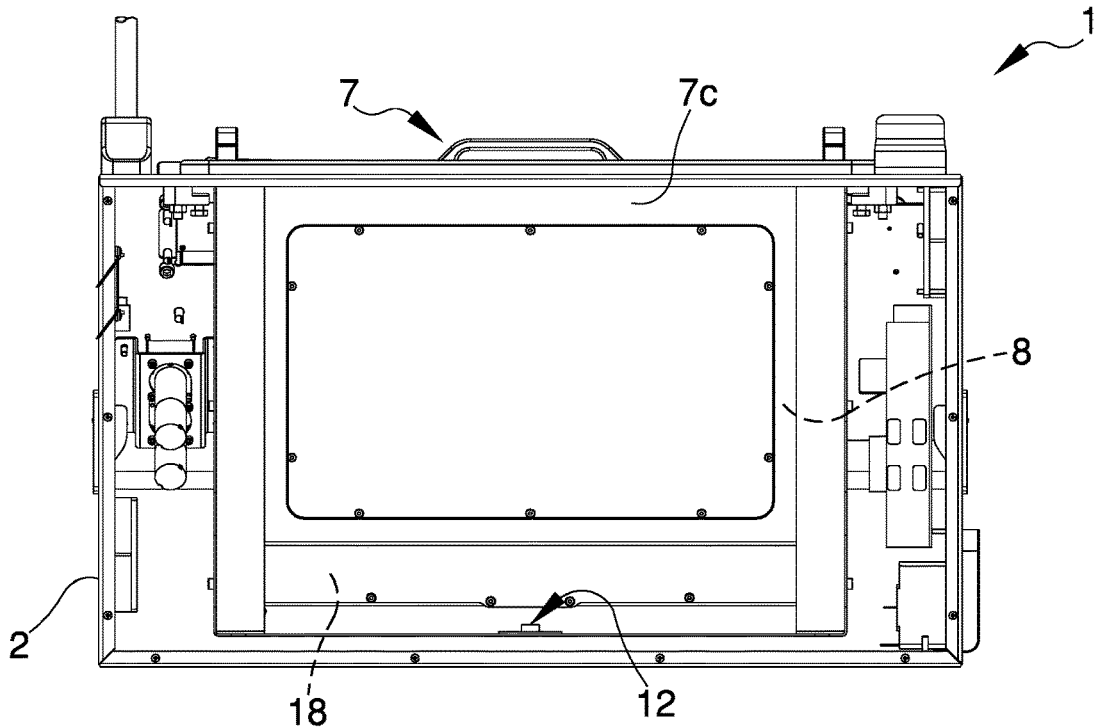
FIG. 5 is a rear elevation view of the machine in FIG. 1.
Figure 6:
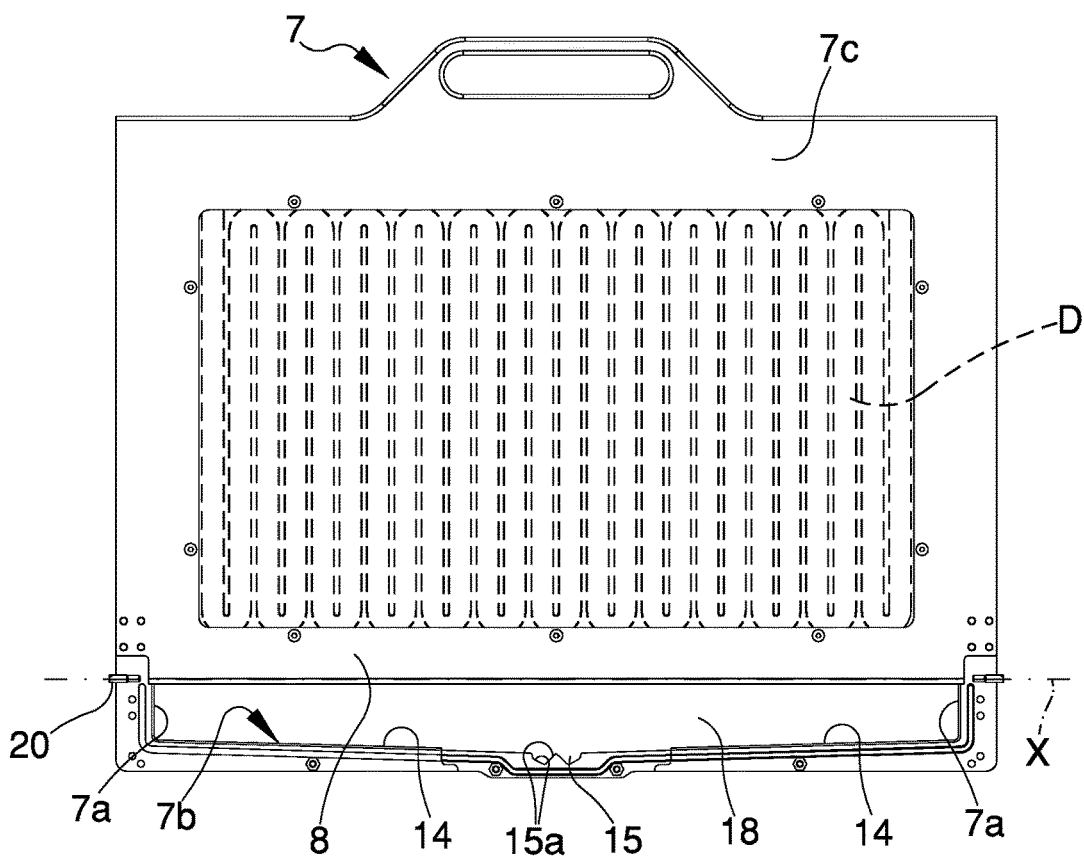
FIG. 6 is a front elevation view of the containment box of the machine in FIG. 1.
Figure 7:
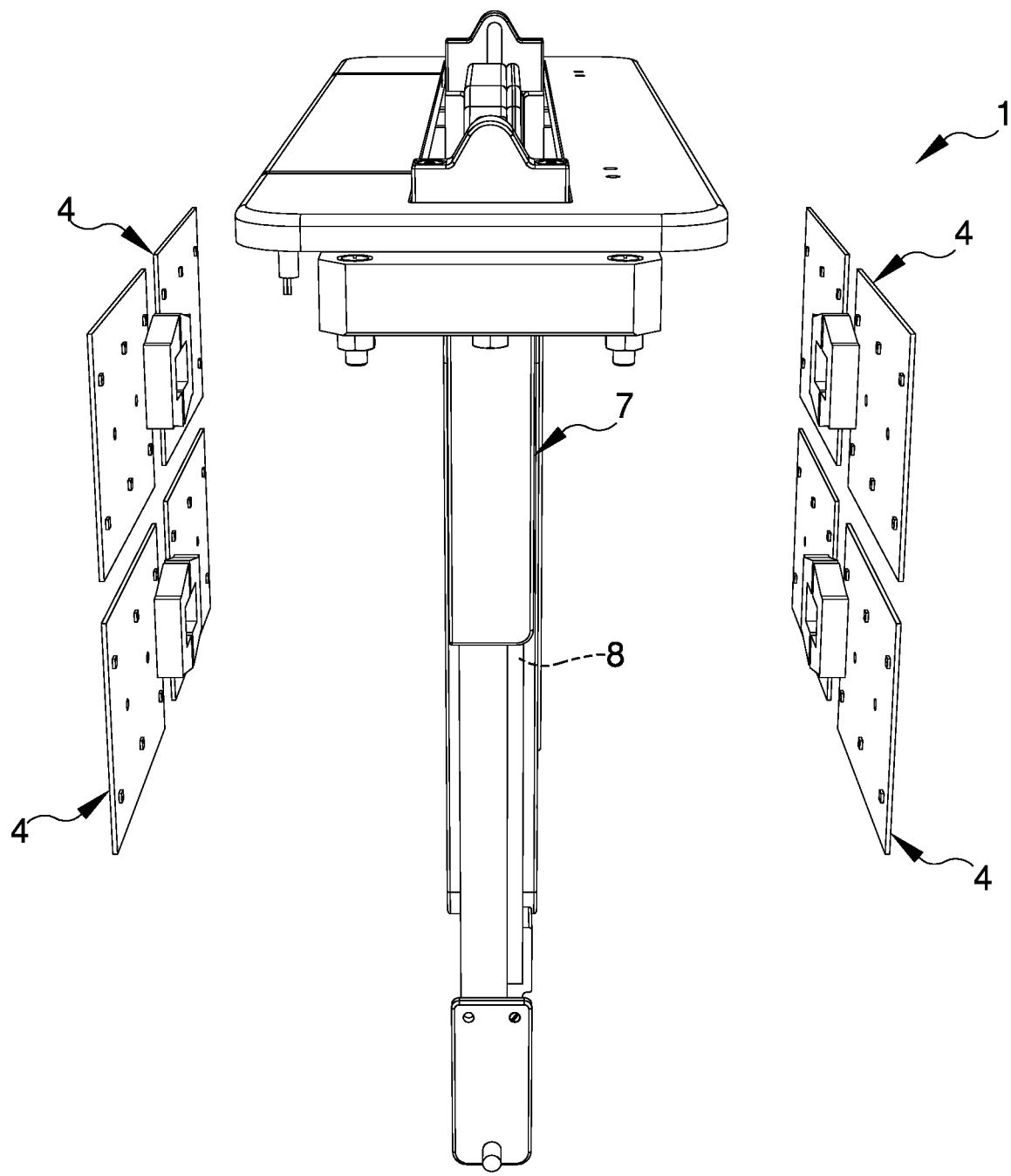
FIG. 7 is an exploded axonometric view of the irradiation means of the machine in FIG. 1.

With particular reference to these figures, reference numeral 1 globally indicates a machine for extracorporeal photopheresis of a biological liquid.

The treated biological liquid is generally a cell concentrate of lymphocytes and mononuclear cells to which a photosensitive drug is added.

The machine 1 comprises a load-bearing body 2 intended to receive a circuit C for the extracorporeal circulation of the biological liquid, where said circuit C comprises at least one bag S containing the biological liquid, at least one collection container D of the biological liquid to be treated, at least one transit duct E of the biological liquid connected at least to the bag S and to the collection container D.

The load-bearing body 2 then supports pumping means 3 of the biological liquid which flows through the transit duct E, e.g. of the type of a peristaltic pump, irradiation means 4 by means of UVA-ray lamps of the collection container D so as to activate the aforementioned photosensitive drug.

Preferably, the irradiation means 4 are of the LED type, which allow for greater wavelength stability of the UVA rays than neon or fluorescent lamps and allow for precise and localized distribution of the relevant beam of light emitted.

Conveniently, the machine 1 also comprises a hematocrit reader 5, closure means 6 of the transit duct E and/or of the portions thereof, which are manually and/or automatically operable to allow/prevent the flow of the operating liquid through them, and pressure detection means 16 adapted to detect the presence of overpressure along the circuit C.

According to the invention, the machine 1 comprises at least one containment box 7 defining a containment volume 8 intended to house the collection container D, and at least one safety chamber 18 arranged below the containment volume 8 and communicating therewith, so as to collect any possible spillage of the biological liquid from the collection container D.

More particularly, the containment box 7 defines a lying plane of the collection container D that is inclined with respect to the horizon, and preferably arranged vertically, whereby the safety chamber 18 is arranged so as to be at a lower level than the containment volume 8.

The containment box 7 defines one or more side walls 7a and at least one bottom wall 7b that delimit, laterally and inferiorly respectively, the safety chamber 18. Superiorly, on the other hand, the safety chamber 18 communicates with the containment volume 8.

In more detail, the side walls 7a and the bottom wall 7b hermetically seal the safety chamber 18.

Conveniently, the volume of the safety chamber 18 is greater than or equal to the volume of the collection container D so as to be able to contain all of the treated biological liquid in the event of a breakage of the collection container itself.

Preferably, the machine 1 comprises detection means 12 for detecting the presence of biological liquid inside the safety chamber 18.

In a preferred embodiment, the detection means 12 comprise at least one sensor of the optical type. In other words, the detection means 12 comprise an emitter of a light beam and a receiver (not visible in detail in the figures) of said light beam, which is then altered in the event of intercepting any droplets of the biological liquid leaked from the collection container D.

Conveniently, the machine 1 is provided with an electronic control unit, not shown in detail in the figures, operatively connected to the detection means 12, and in particular to the relevant receiver. The instant when the luminous signal received by the receiver differs from the standard signal, the electronic control unit is programmed to emit an alarm signal, of an acoustic and/or visual type, and block the operation thereof, e.g. by intervening on the pumping means 3 and/or on the closure means 6.

More particularly, the detection means 12 are arranged outside the safety chamber 18, so that the relevant light beam may intercept the bottom wall 7b. In the embodiment shown in the figures, the light beam emitter 12 is located below the bottom wall 7b. In turn, the bottom wall 7b has at least one portion made of a material which is transparent to light rays, and in particular the portion that is intercepted by the light ray emitted by the emitter 12.

Advantageously, the containment box 7 comprises conveying means 13 of the biological liquid to a collection seat 15 of the biological liquid accessible by the detection means 12.

More specifically, the collection seat 15 is arranged inside the safety chamber 18 and the detection means 12 are arranged in such a way that the relevant light beam can pass through the collection seat itself.

In more detail, the conveying means 13 comprise at least one pair of inclined walls 14, placed inside the safety chamber 18 and converging towards a collection seat 15 of the biological liquid.

In the embodiment shown in the figures, the conveying means 13 are arranged at the point where the bottom wall 7b is located and, in particular, the inclined walls 14 define at least one stretch of the bottom wall 7b.

The collection seat 15 defines a recess with respect to the inclined walls 14 and is bounded by two containment walls 15a which are in turn inclined with respect to the inclined walls 14. In the preferred embodiment shown in the figures, the conveying means 13 comprise two collection seats 15 arranged side by side at the point where the convergence area is located of the inclined walls 14 defining the bottom wall 7b. The emitter 12 is therefore associated with the load-bearing body 2 so as to be arranged, in use, i.e. during the operation of the machine 1, below the collection seat 15.

Advantageously, the containment box 7 is associated in a movable manner with the load-bearing body 2 between at least one operating position, wherein it is arranged at the point where the irradiation means 4 are located, and at least one insertion/removal position, wherein it is moved away from the irradiation means 4 with respect to the operating position to allow the insertion/removal of the collection container D.

In the preferred embodiment shown in the figures, the containment volume 8 is open both laterally and superiorly, so as to allow aeration and cooling of the collection container D during the irradiation phase of the biological liquid contained therein.

In the preferred embodiment shown in the figures, the containment box 7 has a substantially box-shaped conformation and has two containment walls 7c arranged facing the collection container D and arranged on mutually opposite sides thereof.

The containment walls 7c are, in use, arranged facing the irradiation means 4 and made of a transparent material.

Relevant openings are defined between the containment walls 7c at the point where the containment volume 8 is located while, the side walls 7a and the bottom wall 7b are interposed at the point where the safety chamber 18 is located. Different embodiments cannot however be ruled out that provide a different conformation of the containment box 7 while maintaining the same functionality.

Advantageously, the containment box 7 is contained inside the load-bearing body 2 in the operating position and is arranged at least partially outside the load-bearing body in the insertion/removal position.

More particularly, the load-bearing body 2 comprises a housing seat 9 for the housing of the containment box 7, the latter being arranged inside the housing seat 9 in the operating position and at least partially outside the seat itself in the insertion/removal position.

Conveniently, the irradiation means 4 are arranged at the point where the housing seat 9 is located so as to intercept the collection container D, passing through the containment walls 7c, when the containment box 7 is in the operating position.

The detection means 12 described above are arranged below the collection seat 15 when the containment box 7 is in the operating position.

Preferably, the containment box 7 comprises at least one openable portion 10 to allow access to the containment volume 8. The openable portion 10 is movable between an open configuration, wherein it allows the placement/removal of the collection container D in/from the containment volume 8, and a closed configuration wherein the containment volume 8 is inaccessible from the outside.

More specifically, the openable portion 10 is movable between the open configuration and the closed configuration when the containment box 7 is in the insertion/removal position.

In the embodiment shown in the figures, the openable portion 10 is defined at the point where a containment wall 7c is located.

Appropriately, inside the containment box 7 are provided a plurality of retaining elements 11, also referred to as pins, intended to interact with the collection container D to constrain the position thereof inside the containment volume 8.

The containment box 7 is associated at least in a sliding manner with the load-bearing body 2 between the operating position and a home position, wherein it is arranged at least partially outside the housing seat 9 and is substantially aligned with the position taken by the containment box itself in the operating position.

In a particular embodiment, the home position may correspond to the insertion/removal position.

In the preferred embodiment shown in the figures, the containment box 7 is associated movable in rotation with the load-bearing body 2 between the home position and the insertion/removal position.

More particularly, in this embodiment, the load-bearing body 2 has two slots (not visible in detail in the figures) having an elongated shape opposite each other, inside which relevant pivots 20 associated with the containment box 7 are engaged. The pivots 20, sliding along the relevant slots, therefore allow the movement of the containment box 7 from the operating position to the home position and vice versa, while due to the effect of the rotation around the relevant axis X they allow the displacement from the home position to the insertion/removal position and vice versa.

Advantageously, the lying plane defined by the containment box 7, and in particular by the containment volume 8, is arranged substantially vertically in the operating position.

In the embodiment shown in the figures, the lying plane defined by the containment box 7 is then arranged substantially horizontally in the insertion/removal position.

The operation of the present invention is as follows.

After the circuit C has been prepared and assembled, together with the bag S containing the biological liquid, the collection container D is inserted into the containment box 7.

This operation is carried out by moving the containment box 7 from the operating position, wherein it is initially located, to the insertion/removal position.

In particular, the containment box 7 is made to slide with respect to the load-bearing body 2 so as to bring it from the operating position to the home position, after which it is made to rotate around the axis X defined by the pivots 20 to bring it to the insertion/removal position.

After the insertion/removal position has been reached, the openable portion 10 is moved from the closed configuration to the open configuration so as to make the containment volume 8 accessible.

This way, the collection container D can be inserted inside the containment volume 8 and blocked by means of the retaining elements 11.

Next, the openable portion 10 is returned to the closed position and the containment box 7 is returned to the operating position.

At this point the photopheresis treatment can be started, so by acting on the pumping means 3 and on the closure means 6 the biological liquid is made to flow through the circuit C and, therefore, also inside the collection container D.

During operation, the collection container D is irradiated by means of the irradiation means 4, so as to activate the photosensitive drug contained in the biological liquid.

The biological liquid, after being treated, is then reinfused into the patient.

In the event of, during treatment, a breakage occurring in the collection container D, the spilling biological liquid falls towards the inclined walls 14 that convey it to the collection seat 15, where it is identified by the detection means 12.

In this case, as a result of the signal received by the detection means 12, the electronic control unit sends an alarm signal and interrupts the machine operation.

The biological liquid that may flow out of the collection container D is then collected inside the safety chamber 18 which, being hermetically sealed by the side walls 7a and by the bottom wall 7b, prevents it from escaping to the outside.

It has in practice been ascertained that the described invention achieves the intended objects and, in particular, it has been underlined that the photopheresis machine which the present invention relates to, thanks to the presence of a containment box defining a relevant containment volume and a safety chamber placed below the containment volume itself, allows safeguarding the operators and the various components of the machine from contamination by the biological liquid, potentially infected, in case of leakage of the same from the relevant collection container.

In particular, the safety chamber makes it possible to hermetically contain the biological liquid that accidentally or defectively flows out of the relevant collection container. At the same time, the detection means make it possible to quickly detect the leakage of biological liquid and to interrupt the operation of the machine.

Furthermore, the possibility of moving the containment box between the operating position and the insertion/removal position allows promoting, on the one hand, the introduction of the collection container inside it and, on the other hand, to keep the latter in a vertical position during irradiation, so as to optimize the irradiation process.

The invention claimed is:

1. A machine for the extracorporeal photopheresis of a biological liquid, the machine comprising:
   a load-bearing body intended to receive a circuit for the extracorporeal processing of a biological liquid, where said circuit comprises at least one bag containing the biological liquid, at least one collection container of the biological liquid to be treated, at least one transit duct of the biological liquid connected to at least said bag and to said collection container;
   pumping means of the biological liquid crossing said transit duct;
   irradiation means comprising a UVA source; and
   at least one containment box defining a containment volume intended to house said collection container and at least one safety chamber arranged below said containment volume and communicating therewith, so as to collect any possible spillage of the biological liquid from the collection container where said safety chamber has at least one bottom wall and two side walls at which the safety chamber is sealed, wherein
   the containment volume is open both laterally and superiorly, so as to allow aeration and cooling of the collection container during the irradiation phase of the biological liquid contained therein,
   said containment volume communicates with the outside at least laterally and superiorly,
   the volume of said safety chamber is greater than or equal to the volume of said collection container,
   said containment box is movable relative to said load-bearing body between at least one operating position, wherein the containment box is arranged at the point where said irradiation means are located, and at least one insertion/removal position, wherein the containment box is moved away from said irradiation means with respect to the operating position to allow the insertion/removal of the collection container,
   said containment box is configured to slide relative to said load-bearing body between said operating position and a home position wherein the containment box is arranged at least partially outside a housing seat and is substantially aligned with the position taken by the containment box itself in the operating position,
   said containment box is configured to rotate relative to said load-bearing body between said home position and said insertion/removal position,
   said containment box defining a lying plane of the collection container arranged substantially vertical in the operating position,
   said lying plane is arranged substantially horizontally in the insertion/removal position, and
   the safety chamber is separated from the containment volume.

2. The machine according to claim 1, further comprising: detection means of the presence of biological liquid inside said safety chamber.

3. The machine according to claim 2, wherein said detection means comprise at least one optical sensor.

4. The machine according to claim 2, wherein said detection means are arranged outside said safety chamber, below said bottom wall.

5. The machine according to claim 4, wherein said bottom wall has at least one portion made of a material which is transparent to light rays.

6. The machine according to claim 3, wherein said containment box comprises conveying means of the biological liquid to a collection seat of the biological liquid accessible by said detection means.

7. The machine according to claim 6, wherein said conveying means comprise at least one pair of inclined walls, placed inside said safety chamber and converging towards said collection seat.

8. The machine according to claim 7, wherein said collection seat defines a recess with respect to said inclined walls.

9. The machine according to claim 7, wherein said inclined walls define said bottom wall.

10. The machine according to claim 1, wherein said containment box is contained inside said load-bearing body in the operating position and is arranged at least partially outside said load-bearing body in the insertion/removal position.

11. The machine according to claim 1, wherein said load-bearing body comprises the housing seat for the housing of said containment box, the containment box being arranged inside said housing seat in the operating position and at least partially outside said seat itself in the insertion/removal position, and wherein said irradiation means being arranged beneath said housing seat, such that the housing seat suspends the containment box in front of the irradiation means.

12. The machine according to claim 1, wherein said containment box comprises at least one openable portion to allow the access to said containment volume, said openable portion being movable between an open configuration and a closed configuration with said containment box in the insertion/removal position.

13. The machine according to claim 1, wherein said irradiation means comprise LBDs.

* * * * *